(12) United States Patent
Gray (10) Patent No.: US 6,277,069 B1
(45) Date of Patent: *Aug. 21, 2001

(54) CLAMPING DEVICE

(75) Inventor: Bruce Nathaniel Gray, Claremont (AU)

(73) Assignee: Pine Ridge Holding Pty. Ltd., Claremont (AU)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/326,110

(22) Filed: Jun. 4, 1999

(30) Foreign Application Priority Data

Jun. 9, 1998 (AU) .................................................. PP 3965

(51) Int. Cl.[7] ...................................................... A61B 1/32
(52) U.S. Cl. ............................................ 600/234; 403/391
(58) Field of Search .................................... 600/230, 234, 600/201, 227; 403/391, DIG. 9, DIG. 8

(56) References Cited

U.S. PATENT DOCUMENTS

| | | | |
|---|---|---|---|
| 3,046,072 | * 7/1962 | Douglass, Jr. et al. | 600/230 X |
| 3,572,326 | * 3/1971 | Jensen | 600/234 X |
| 3,810,462 | * 5/1974 | Szpur | 600/234 |
| 5,727,899 | 3/1998 | Dobrovolny | 403/389 |
| 5,792,046 | 8/1998 | Dobrovolny | 600/234 |
| 5,888,197 | 3/1999 | Mulac et al. | 600/234 |

OTHER PUBLICATIONS

Translation of French Patent Document FR 2732887.

* cited by examiner

Primary Examiner—Jeffrey A. Smith
(74) Attorney, Agent, or Firm—Davidson, Davidson, Kappel, LLC (57) ABSTRACT

A clamping device (10) for clampingly interconnecting a first elongate element (17) and a second elongate element (15). The clamping device (10) comprises a shaft (19), and a first clamping member (21) mounted on the shaft. The first clamping member (21) has first and second clamping sections (31, 32) between which the first elongate element (17) can be slidingly received and clampingly engaged. An aperture (73) is provided in the shaft (19) adjacent the second section (32) of the first clamping member (21) to slidingly receive the second elongate member (15). A second clamping member (22) is mounted on the shaft (19) and is displaceable therealong for clamping the second elongate element (15) between the first clamping member (21) and the second clamping member (22). A cam locking mechanism (23) is operably connected to the shaft (19) for selectively moving the clamping device between clamping and non-clamping conditions. In moving the clamping device (10) into the clamping condition, the cam locking mechanism (23) causes displacement of the second clamping member (22) along the shaft (19) such that the second elongate element (15) is clampingly engaged between the first clamping member (21) and the second clamping member (22).

15 Claims, 7 Drawing Sheets

CLAMPING DEVICE

BACKGROUND OF THE INVENTION

The present invention relates to a clamping device for interconnecting two elongate elements.

The clamping device has been devised particularly, although not necessarily solely, for use with surgical retractors.

In surgical operations requiring access to internal organs and bone structures, it is common to use retractors to hold back tissue about the surgical site, so as to expose the area in which surgery is to be performed. Typically, a retractor includes a retractor blade which engages the tissue, and a retractor shaft onto which the retractor blade is mounted. The retractor is attached to a retractor support structure by some form of clamping device. The retractor support structure typically includes a rail which the clamping device can engage to thereby connect the retractor to the retractor support structure.

It is important that the clamping devices allow the retractors to be conveniently positioned on the retractor support structure and to be conveniently adjusted as necessary to achieve appropriate positioning with respect to the surgical site. Additionally, it is important that the clamping devices should not pose any significant obstruction to access to the surgical site and to movement of personnel about the surgical site, during the surgical procedure.

Various types of clamping devices have been proposed including those disclosed in U.S. Pat. Nos. 5,727,899 (Dobrovolny), 5,792,046 (Dobrovolny) and 5,888,197 (Mulac). Each of those patents discloses a clamping device which includes a first clamping member for releasably engaging a retractor shaft, a second clamping member for releasably engaging a rail forming part of a retractor support structure, and a shaft which extends between the first and second clamping members and which is operable in association with a camming mechanism to cause the first and second clamping members to move between clamping and non-clamping conditions. Each clamping member includes a mounting section which is mounted on the shaft and a clamping section which is offset from the shaft. Typically, the clamping section includes a clamping aperture in which the component undergoing clamping is received. While such arrangements have proved satisfactory in operation, they do suffer from several deficiencies.

One deficiency is that the clamping device does not lend itself to a compact construction owing to the fact that the clamping section of each clamping member is offset with respect to the shaft on which the clamping members are supported.

Secondly, the offset relationship between the shaft of the clamping device and the retractor shaft renders the retractor vulnerable to deflection in the event of accidental impact during the surgical procedure.

Thirdly, cleaning of and sterilisation of the clamping devices is rendered difficult where they contain large numbers of operational parts. Furthermore, it can sometimes be difficult to insert the retractor shaft of a retractor in the clamping aperture of the appropriate clamping member owing to the close tolerances required for the clamping aperture in order for it to effectively move between clamping and non-clamping conditions upon operation of the clamping device. As a result of the close tolerances, there is little opportunity to accommodate misalignment between the retractor shaft and the clamping aperture when the clamping shaft is being presented to the clamping aperture for insertion therein during the process of setting up the retractor system.

It is against this background, and the problems and deficiencies associated therewith, that the present invention has been developed.

SUMMARY OF THE INVENTION

The present invention provides a clamping device for clampingly interconnecting first and second elongate elements, the clamping device comprising a shaft, a first clamping member mounted on the shaft, the first clamping member having first and second clamping sections between which the first elongate element can be slidingly received and clampingly engaged, an aperture in the shaft adjacent the second section of the first clamping member to slidingly receive the second elongate element, a second clamping member mounted on the shaft and being displaceable therealong for clamping the second elongate element between the first clamping member and the second clamping member, and actuation means associated with the shaft for selectively moving the clamping device between clamping and non-clamping conditions.

With this arrangement, the elongate element which is received and clampingly retained in the aperture is generally aligned with the shaft rather than being offset with respect to it.

The actuation means may be adapted to apply a compressive force between the second clamping member and the first section of the first clamping member thereby to cause clamping engagement of the first and second elongate elements.

The actuation means may comprise a cam locking mechanism. The cam locking mechanism may include a cam pivotably connected to the shaft and a handle connected to the cam for pivotally moving the cam between clamping and release positions, wherein during movement towards the clamping position, the cam contacts the second clamping member to cause displacement thereof along the shaft.

Preferably, the first and second sections of the first clamping member are resiliently movable with respect to each other from the clamping condition to the non-clamping condition.

The first clamping member may be of unitary construction whereby the first and second seconds are connected by an integral hinge section.

The second clamping member may comprise a body having an opening through which the shaft is received, the body presenting a clamping face for engagement with the elongate element received in the aperture in the shaft.

The second clamping member may further comprise an abutment member positioned adjacent the body on the side thereof remote from the aperture in the shaft. The abutment member may be formed of a low-friction plastics material. The low-friction material from which the abutment member is formed facilitates sliding contact between the cam and the second mounting member as the cam is moved between the clamping and release positions.

The aperture formed in the shaft is preferably of a size whereby a loose fit is provided between the aperture and the elongate element received therein. Conveniently, the aperture is elongated with the longitudinal axis thereof extending along the longitudinal axis of the shaft. The elongated nature of the aperture contributes to the loose fit and the ease in which the elongate element can be positioned in the aperture.

A stop may be provided on the shaft to limit the extent to which the second mounting member can be displaced along the shaft, so ensuring that the second clamping member does not obstruct the aperture to an extent that it hinders insertion of the elongate member in the aperture.

The end of the shaft remote from the cam locking mechanism is connected to the second section of the first clamping member in any suitable fashion such as by threaded engagement therewith.

The shaft may extend from the first section of the first clamping member and beyond the second clamping member by passing through a hole formed in the second section of the first clamping member.

The present invention further provides a clamping device for clampingly interconnecting first and second elongate elements, the clamping device comprising a shaft, a first clamping member mounted on the shaft, the first clamping member having first and second clamping sections between which the first elongate element can be slidingly received and clampingly engaged, the shaft being connected to the first clamping section and extending beyond the second clamping section, an aperture in the shaft adjacent the second section of the first clamping member to slidingly receive the second elongate element, a second clamping member mounted on the shaft and being displaceable therealong for clamping the second elongate element between the first clamping member and the second clamping member, and a cam locking mechanism operatively connected to the shaft for applying a compressive force between the second clamping member and the first section of the first clamping member thereby to cause clamping engagement of the first and second elongate elements.

The present invention still further provides a clamping device for clamping a retractor shaft to a support rail, the clamping device comprising a shaft, a first clamping member mounted on the shaft, the first clamping member having first and second clamping sections between which the support rail can be slidingly received and clampingly engaged, an aperture in the shaft adjacent the first clamping member to slidingly receive the retractor shaft, and a second clamping member mounted on the shaft and being displaceable therealong for clamping the retractor shaft between the first clamping member and the second clamping member, and actuation means associated with the shaft for selectively moving the clamping device between clamping and non-clamping conditions.

BRIEF DESCRIPTION OF THE DRAWINGS

The invention will be better understood by reference to the following description of one specific embodiment thereof in which.

DETAILED DESCRIPTION OF THE PREFERRED EMBODIMENT

The embodiment shown in the drawings is directed to a clamping device 10 for use in connecting a retractor 11 to a retractor support structure 13. In a typical case, the retractor support structure 13 is used to support one or more of such retractors 11 above an opening table.

Each retractor 11 includes a retractor shaft 15 on one end of which is supported a retractor blade (not shown) which holds back tissue adjacent a surgical site in a patient in known manner so as to provide access to the site. The retractor support structure 11 includes an elongate element which provides a rail 17 onto which the retractor shaft 15 is mounted by way of the clamping device 10. The retractor shaft 15 and the rail 17 are both of circular cross-section.

The clamping device 10 allows the retractor 11 to be adjusted in position with respect to the rail 17 as necessary.

The clamping device 10 comprises a shaft 19, a first clamping member 21 mounted on the shaft 19 and a second clamping member 22 also mounted on the shaft 19. The clamping device 10 further comprises a cam locking mechanism 23 operatively connected to the shaft 19 for moving the clamping device between non-clamping and clamping conditions, as will be explained in detail later.

The first clamping member 21 comprises a clamping body 27 which is of unitary construction and which has an inner face 28 and an outer face 29. The clamping body 27 includes a first clamping section 31 and a second clamping section 32 connected together at one end thereof by a section which provides an integral hinge 33. A clamping aperture 35 is provided in the end of the clamping body 27 remote from the integral hinge 33. A gap 37 defined between the upper and lower clamping sections 31 and 32 respectively extends between the clamping aperture 35 and a bore 39 in the body adjacent the hinge 33. The bore 39 serves to assist operation of the integral hinge 33. The gap 37 allows the two clamping sections 31, 32 to resiliently flex with respect to each other about the integral hinge 33, thereby expanding and contracting the clamping aperture 35.

The resilient nature of the clamping body 27 biasses the clamping aperture 35 into the expanded condition. The clamping aperture 35 is defined by two recesses 41, one formed in the first clamping section 31 and the other formed in the second clamping section 32. The recesses 41 define an arcuate jaw which is of a configuration accommodating the circular rail 17 and which has a mouth 42. A bevel 43 is provided adjacent each recess 41 to provide a guide surface for guiding the rail 17 into the clamping aperture. The rail 17 can enter the clamping aperture 35 sidewardly through the mouth 42 when the clamping aperture 35 is in the expanded condition, as indicated by arrow 44 in FIG. 5.

The first clamping member 21 has a bore 47 extending through the clamping body 27. The bore 47 provides a first hole 51 in the first clamping section 31 and a second hole 52 in the second clamping section 32.

The shaft 19 includes a male threaded section 53 at one end thereof, a lug section 55 at the other end thereof, and an intermediate shank section 57 between the threaded section 53 and the lug section 55. A step 59 is provided at the junction between the intermediate section 57 and the threaded section 53.

Figure 3:
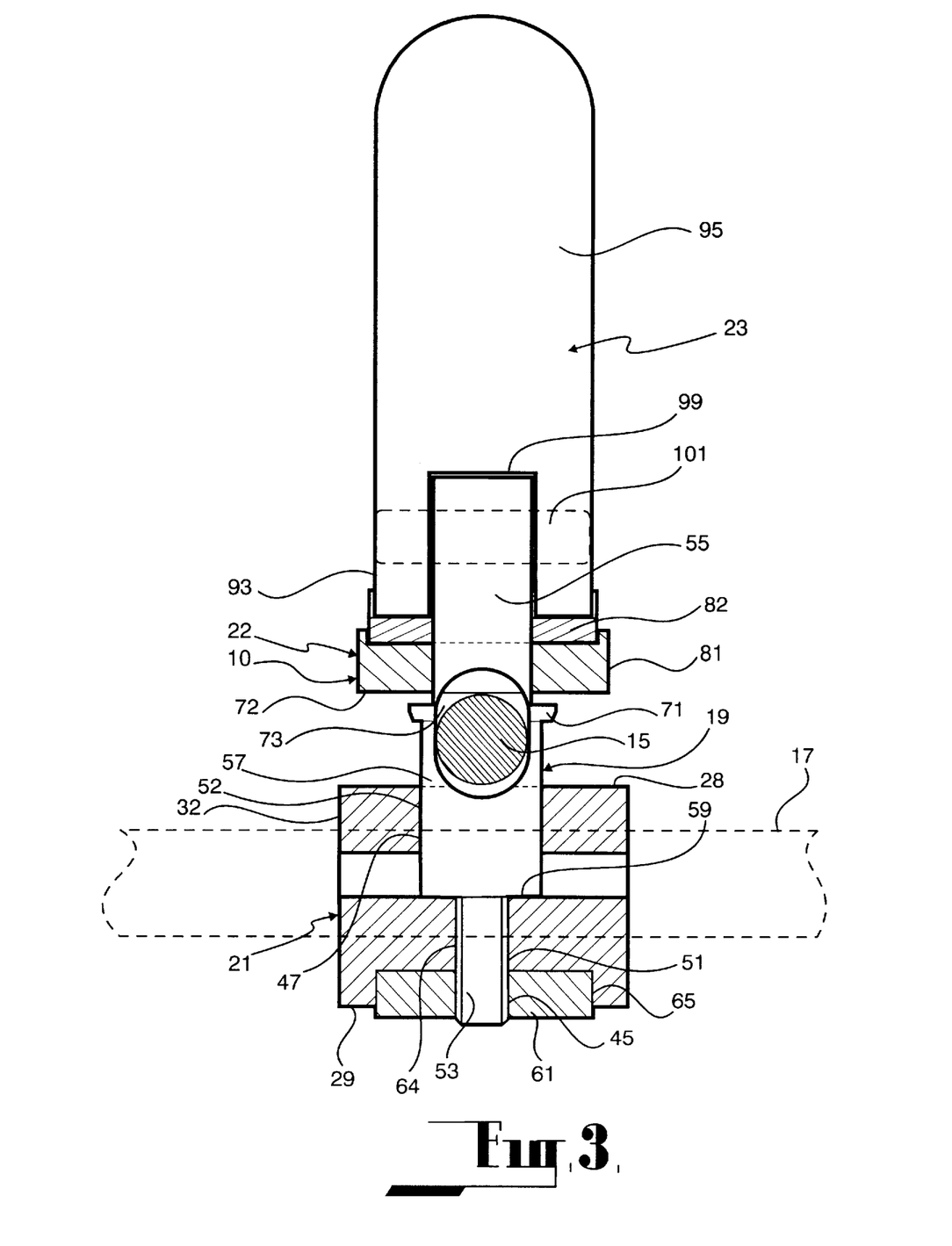
FIG. 3 is a sectional elevation of the clamping device shown in a non-clamping condition.

The threaded connection 45 between the shaft 19 and the first clamping section 31 is provided by a retainer 61 which threadingly engages the threaded section 53 of the shaft 19. The threaded section 53 of the shaft 19 is received in, and projects beyond, the first hole 51 of the first clamping section 31, as seen in FIG. 3 of the drawings. The step 59 on the shaft 19 bears on the inner face of the first clamping section 31. The retainer 61 is accommodated within a recess 65 formed in the outer face 29 of the first clamping section 31. With this arrangement, the shaft 19 is engaged to the first clamping section 31 of the first clamping member 21.

The intermediate section 57 of the shaft 19 extends through the second hole 52 in the second clamping section 32 without being connected thereto so as to allow the first and second clamping sections 31, 32 to flex resiliently with respect to each other without interference by the shaft 19.

The first hole 51 provides a bore 64 of reduced size to accommodate the threaded section 53 of the shaft 19.

The second clamping member 22 is slidably positioned on the shaft 19. More particularly, the second clamping member 22 is slidably positioned on the lug section 55 of the shaft and has a central hole 67 through which the lug section is received. With this arrangement, the second clamping portion 22 can undergo limited displacement along the shaft 19. The extent to which the second clamping member 22 can be displaced along the shaft 19 in the direction towards the first clamping member 21 is limited by a stop 71 in the form of a collar formed integrally on the shaft.

The second clamping member 22 presents a clamping face 72.

Figure 4:
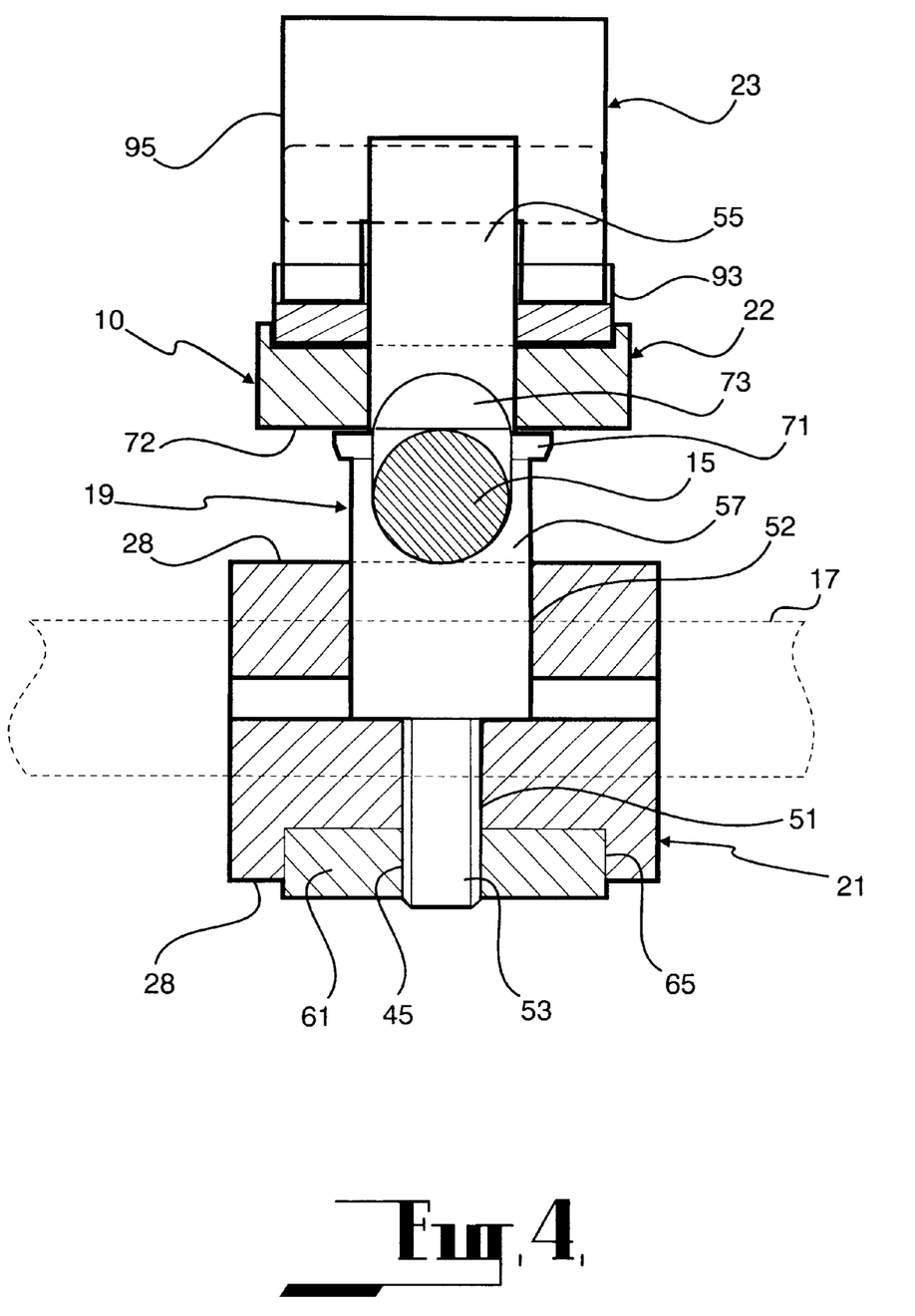
FIG. 4 is a view similar to FIG. 3 with the exception that the clamping device is shown in a clamping condition.

An aperture 73 is provided in the shaft 19 and is so positioned such that it is immediately adjacent the inner face 28 of the first clamping member 21, as well as generally between the first clamping member 21 and the second clamping member 22, (as best seen in FIGS. 3 and 4 of the drawings). The aperture 73 is of a size whereby it can receive the retractor shaft 15 with a loose fit. Indeed, the aperture 73 is elongated in the longitudinal direction of the shaft 19 so as to provide the loose fit. The loose fit is provided to assist insertion of the retractor shaft 15 into the aperture 73.

With the retractor shaft 15 received in the aperture 73, the retractor shaft 15 can be clamped between the first clamping member 21 and the second clamping member 22. More particularly, the retractor shaft 15 is clamped between the inner face 28 on the first clamping member 21 and the clamping face 72 on the second clamping member 22.

The stop 71 limits the extent to which the second clamping member 22 can move along the shaft 19 into a position in which it covers the aperture 73. Even with the second clamping member 22 displaced into a condition in which it bears against the stop 71, the aperture 73 is sufficiently exposed to allow access for insertion of the retractor shaft 15. In the absence of the stop 71, it is likely that the second clamping member 22 would locate against the first clamping member 21 and thereby interfere with insertion of the retractor shaft 15 in the aperture 73.

The second clamping member 22 comprises a first portion 81 and a second portion 82. The first portion 81 is formed of rigid material such as stainless steel and presents the clamping face 72. The first portion 81 is of generally cylindrical construction and incorporates a recess 83 in which the second portion 82 can locate. The second portion 82 is formed of low-friction plastics material and incorporates a cradle 85, the purpose of which will be explained later.

The cam locking mechanism 23 is operatively connected to the shaft 19 for providing a compressive force in association with the shaft 19 between the second clamping member 22 and the first clamping section 31 of the first clamping member 21. This compressive force acts to contract the clamping aperture 35 in the first clamping member 21 thereby to clampingly engage the rail 17, and to displace the second clamping member 22 along the shaft 19 towards the first clamping member 21 thereby to clampingly engage the retractor shaft 15 within the aperture 73.

The cam locking mechanism 23 comprises a cam 93 which is pivotably connected to the shaft 19, and a handle 95 formed integrally with the cam. The handle 95 provides a lever for operating the cam.

The cam 93 comprises two cam sections 97 between which there is a gap 99. The cam 93 is positioned on the shaft 19 with the outer end of the lug section 55 of the shaft 19 received in the gap 99 of the cam. A pivot pin 101 extends through aligned apertures 103, 105 in the cam 93 and the lug section 55 respectively. In this way, the pivot pin 101 pivotally connects the cam 93 to the shaft 19.

Figure 5:
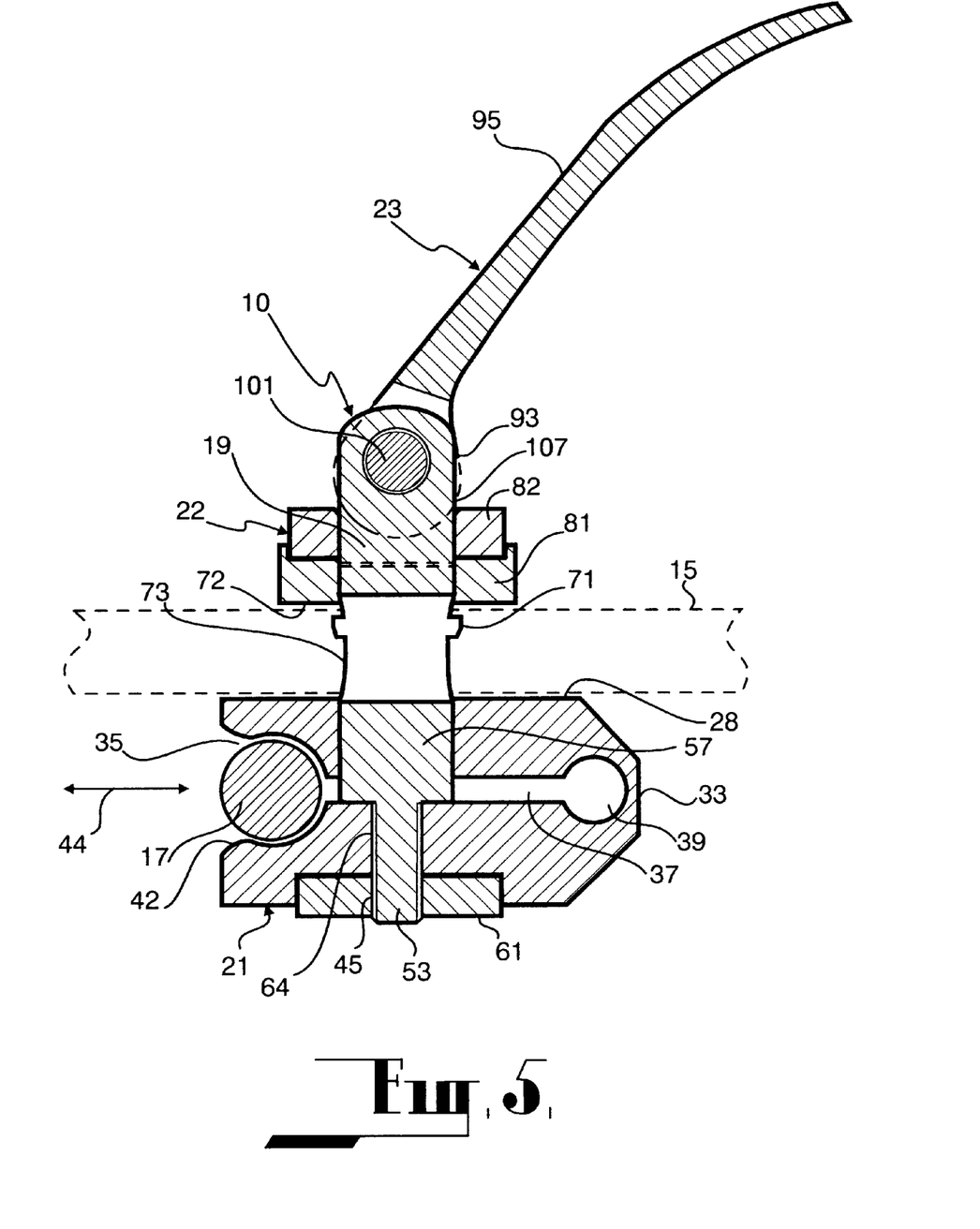
FIG. 5 is a sectional side view of the clamping device shown in a non-clamping condition.
Figure 6:
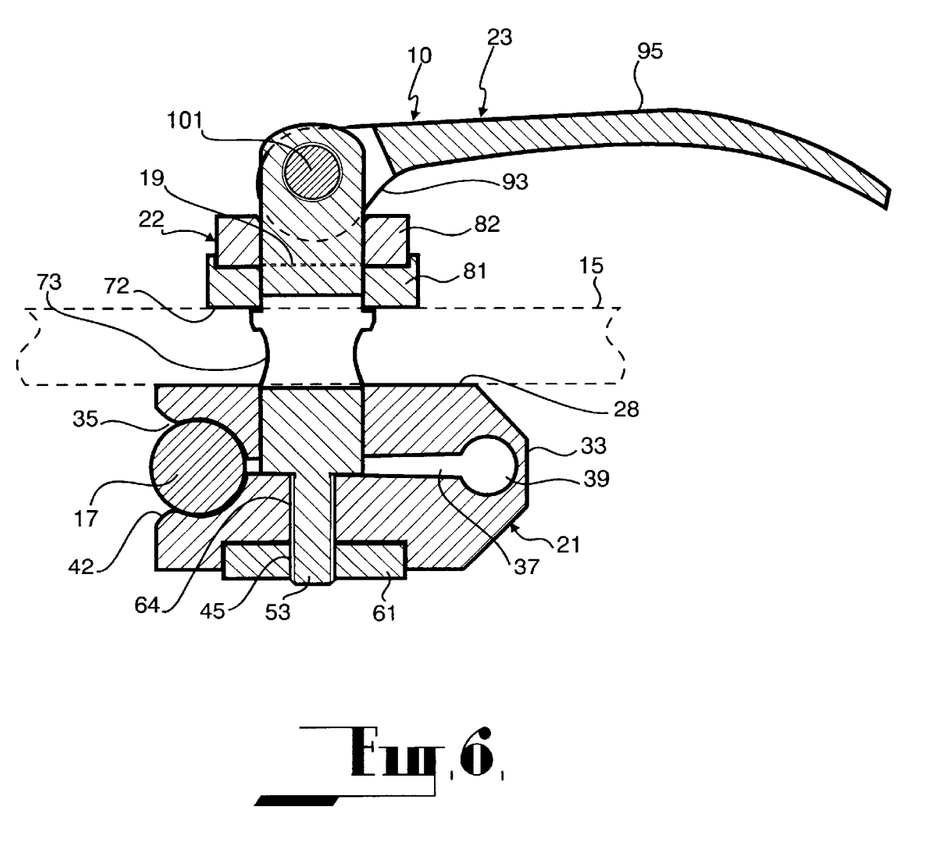
FIG. 6 is a view similar to FIG. 5 with the exception that the clamping device is shown in a clamping condition.
Figure 7:
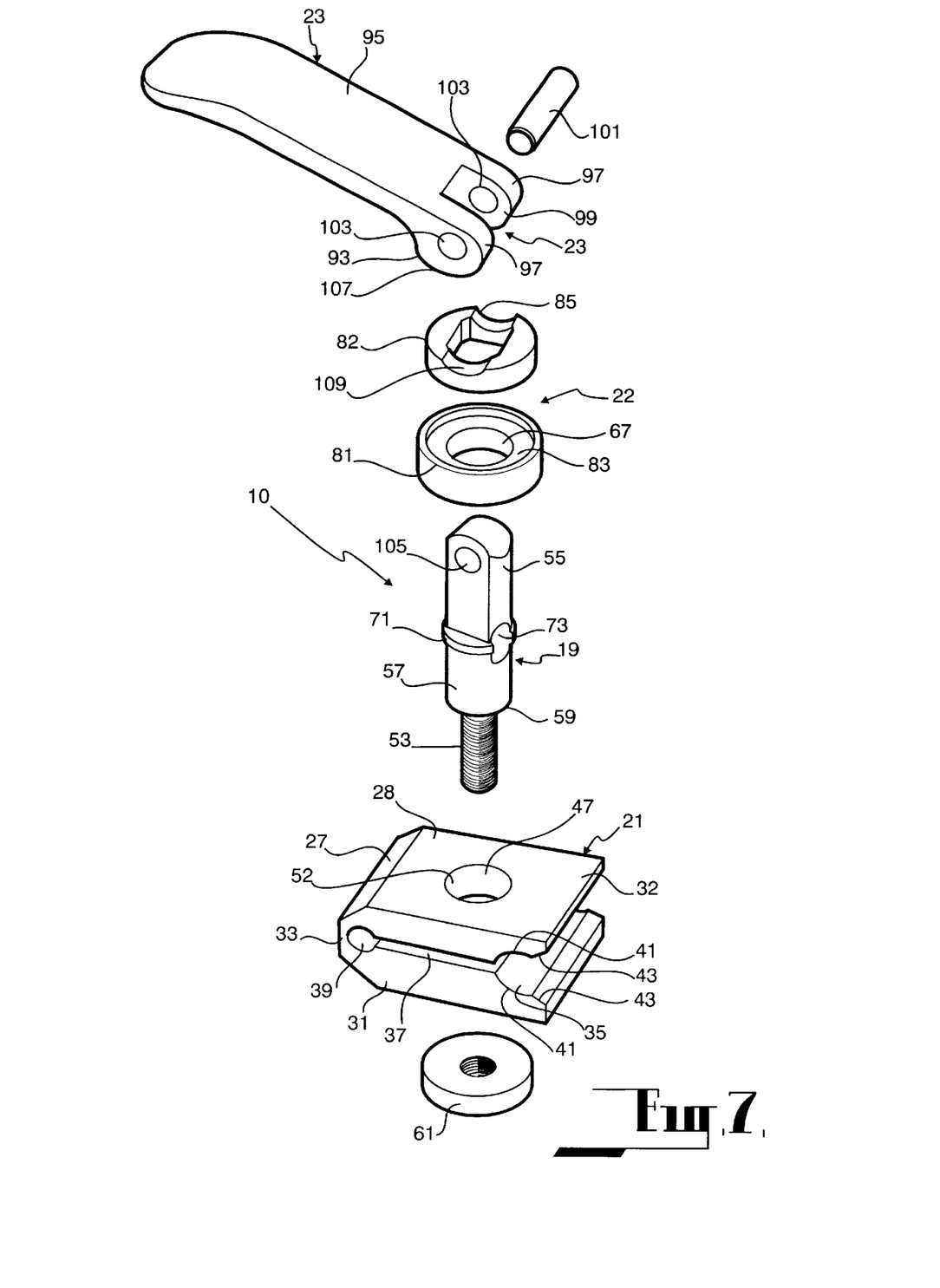
FIG. 7 is an exploded view of the clamping device.

The cam 93 is accommodated in the cradle 85 within the second portion 82 of the second clamping member 22. The cam 93 has a cam surface 107 which co-acts with the surface 109 of the cradle 85 to cause displacement of the second clamping member 22 upon movement of the cam 93 from a release condition (as shown in FIGS. 3 and 5) to a locking condition (as shown in FIG. 4 and 6).

Figure 1:
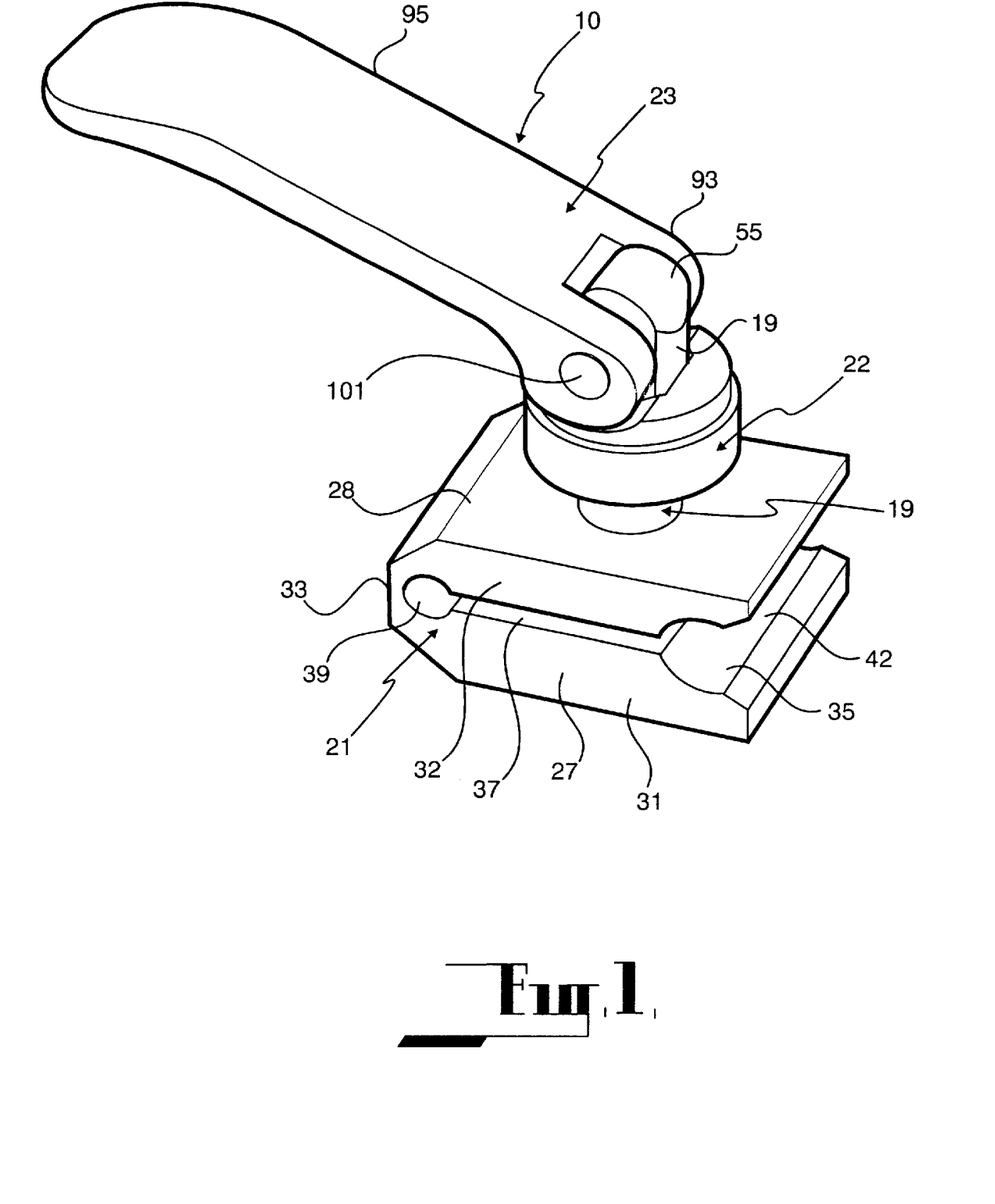
FIG. 1 is a perspective view of a clamping device according to the embodiment.
Figure 2:
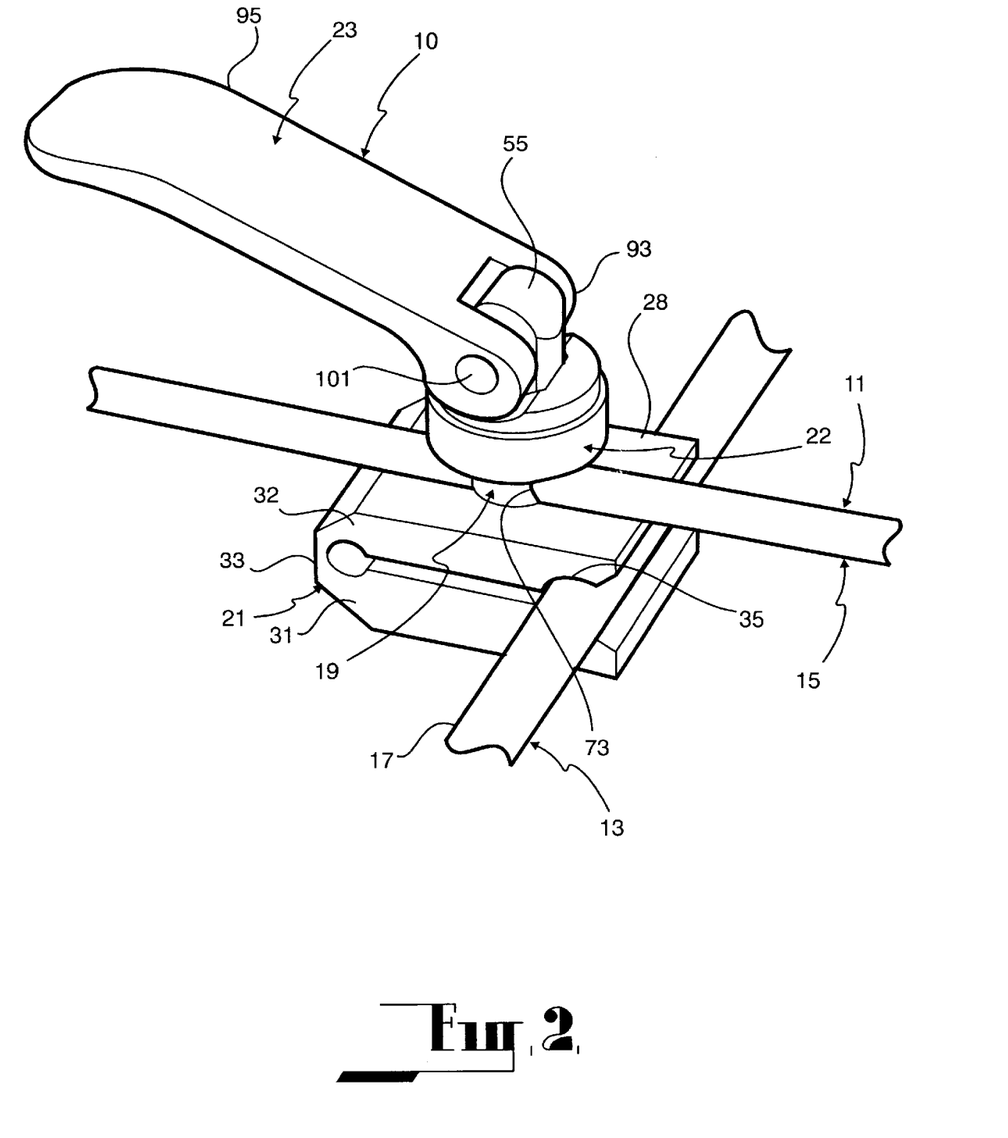
FIG. 2 is a view similar to FIG. 1 with the exception that the clamping device is showing connecting a retractor shaft to a support rail of a retractor support structure.

The axis of rotation of the cam 93 about the pin 101 is normal to the central axis of the aperture 73. In this way, the longitudinal extent of the handle 95 is generally in the same direction as the retractor shaft 15 when the cam is in the locking condition, as best seen in FIGS. 2 and 6 of the drawings. This is particularly advantageous in that it promotes a compact arrangement when the clamping device 10 is in a clamping condition, thereby reducing the opportunity for the clamping device to pose a significant obstruction to a surgeon and other attendants conducting a surgical procedure.

The clamping device 10 according to the embodiment provides a simple yet highly effective arrangement for securely mounting the retractor shaft 15 onto the rail 17 of the retractor support structure. With the clamping device 10 in a non-clamping condition, the first clamping member 21 is positioned on the rail 17 of the retractor support structure, with the rail received in the clamping aperture 35. The retractor shaft 15 is then positioned within the aperture 73 such that it is between the first clamping member 21 and the second clamping member 22. The position of the retractor blade (not shown) can be adjusted with respect to the surgical site as necessary by various actions including linear and angular adjustment of the clamping device is with respect to the rail 17, and linear and angular adjustment of the retractor shaft 15 with respect to the clamping device 10. Once the retractor blade is in the required position, the cam locking mechanism 23 can be operated so as to move the clamping device 10 from the non-clamping condition to the clamping condition. In the clamping condition, the first clamping member 21 clampingly engages the rail 17, and the first and second clamping members 21 and 22 respectively cooperate to clampingly engage the retractor shaft 15.

Upon subsequent release of the cam locking mechanism 23, the resilient nature of the first clamping member 21 causes expansion of the clamping aperture 35 to release the rail 17 from the clamping condition. This also allows displacement of the second clamping member 22 away from the first clamping member 21 so as to release the retractor shaft 15 from the clamping condition.

A particular advantage of the clamping device according to the embodiment is that the retractor shaft 15 is generally aligned with the shaft 19 of the clamping device. This is beneficial in that any accidental knock or impact against the retractor during a surgical procedure is less likely to cause the retractor to swing about the shaft 19 and move the retractor blade out of position. Furthermore, it provides for a more compact construction as compared to the prior art devices described previously.

A still further advantage of the clamping device according to the embodiment is that the clamping force applied by the cam locking mechanism 23 is along the line of the shaft 19. In this way, a clamping force transferred through the clamping device 10 is applied to the retractor shaft 15 along the line of action of the force and so provides for a more effective clamping action.

The clamping device according to the embodiment can be constructed of any suitable material. A particularly suitable material is stainless steel, which is used throughout the embodiment apart from the second portion 82 of the second clamping member 22 which is of plastics material.

From the forgoing, it is evident that the present embodiment provides a simple yet highly effective clamping device for releasably interconnecting first and second elongate elements.

It should be appreciated that the scope of the invention is not limited to the scope of the embodiment described. In particular, it should be appreciated that the clamping device according to the invention can be used to clampingly interconnect any suitable elongate elements and that it is not restricted to clamping elongate elements in the form of retractor shafts and rails of retractor support structures.

What is claimed is:

1. A clamping device for clampingly interconnecting first and second elongate elements, the clamping device comprising a shaft, a first clamping member mounted on the shaft, the first clamping member having first and second clamping sections between which the first elongate element can be slidingly received and clampingly engaged, an aperture in the shaft adjacent the second section of the first clamping member to slidingly receive the second elongate member, a second clamping member mounted on the shaft and being displaceable therealong for clamping the second elongate element between the first clamping member and the second clamping member, and actuation means associated with the shaft for selectively moving the clamping device between clamping and non-clamping conditions.

2. A clamping device according to claim 1, wherein the actuation means is adapted to apply a compressive force between the second clamping member and the first section of the first clamping member thereby to cause clamping engagement of the first and second elongate elements.

3. A clamping device according to claim 2 wherein the actuation means comprises a cam locking mechanism.

4. A clamping device according to claim 3 wherein the cam locking mechanism includes a cam pivotably connected to the shaft and a handle connected to the cam for pivotally moving the cam between clamping and release positions, wherein during movement towards the clamping position the cam contacts the second clamping member to cause displacement thereof along the shaft.

5. A clamping device according to claim 1 wherein the first and second sections of the first clamping member are resiliently movable with respect to each other from the clamping condition to the non-clamping condition.

6. A clamping device according to claim 5 wherein the first clamping member is of unitary construction whereby the first and second sections are connected together by an integral hinge section.

7. A clamping device according to claim 1 wherein the second clamping member comprises a body having an opening through which the shaft is received, the body presenting a clamping face for engagement with the elongate element received in the aperture in the shaft.

8. A clamping device according to claim 7 wherein the second clamping member further comprises an abutment element positioned adjacent the body on the side thereof remote from the aperture in the shaft.

9. A clamping device according to claim 8 wherein the abutment member is formed of low-friction plastics material.

10. A clamping device according to claim 1 wherein the aperture formed in the shaft is of a size whereby a loose fit is provided between the aperture and the elongate element received therein.

11. A clamping device according to claim 10 wherein the aperture is elongated with the longitudinal axis thereof extending along the longitudinal axis of the shaft.

12. A clamping device according to claim 1 wherein a stop is provided on the shaft to limit the extent to which the second mounting member can be displaced along the shaft.

13. A clamping device according to claim 1 wherein the shaft is threadingly connected to the first clamping section.

14. A clamping device for clampingly interconnecting first and second elongate elements, the clamping device comprising a shaft, a first clamping member mounted on the shaft, the first clamping member having first and second clamping sections between which the first elongate element can be slidingly received and clampingly engaged, the shaft being connected to the first clamping section and extending beyond the second clamping section, an aperture in the shaft adjacent the second clamping section of the first clamping member to slidingly receive the second elongate member, a second clamping member mounted on the shaft and being displaceable therealong for clamping the second elongate element between the first clamping member and the second clamping member, and a cam locking mechanism operatively connected to the shaft for applying a compressive force between the second clamping member and the first clamping section of the first clamping member thereby to cause clamping engagement of the first and second elongate elements.

15. A clamping device for clamping a retractor shaft to a support rail, the clamping device comprising a shaft, a first clamping member mounted on the shaft, the first clamping member having first and second clamping sections between which the support rail can be slidingly received and clampingly engage, an aperture in the shaft adjacent the first clamping member to slidingly receive the retractor shaft, a second clamping member mounted on the shaft and being displaceable therealong for clamping the retractor shaft between the first clamping member and the second clamping member, and actuation means associated with the shaft for selectively moving the clamping device between clamping and non-clamping conditions.

* * * * *